(12) United States Patent
Schiff et al.

(10) Patent No.: US 11,426,523 B1
(45) Date of Patent: Aug. 30, 2022

(54) DRUG DELIVERY ASSEMBLY INCLUDING A REMOVABLE CARTRIDGE

(71) Applicant: Fresenius Kabi Deutschland GmbH, Bad Homburg (DE)

(72) Inventors: David R Schiff, Highland Park, NJ (US); Sharon D West, Elkins Park, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/180,578

(22) Filed: Feb. 19, 2021

(51) Int. Cl.
*A61M 5/315* (2006.01)
*A61M 5/142* (2006.01)

(52) U.S. Cl.
CPC .... *A61M 5/31501* (2013.01); *A61M 5/14248* (2013.01); *A61M 5/31585* (2013.01); *A61M 2005/14252* (2013.01); *A61M 2005/14268* (2013.01); *A61M 2202/0007* (2013.01); *A61M 2209/088* (2013.01)

(58) Field of Classification Search
CPC .... A61M 5/14248; A61M 2005/14252; A61M 2005/14268; A61M 5/28; A61M 5/285; A61M 5/288; A61M 5/31501; A61M 5/3287
See application file for complete search history.

(56) References Cited

U.S. PATENT DOCUMENTS

| 2003/0167036 A1 | 9/2003 | Flaherty |
| 2012/0010594 A1* | 1/2012 | Holt ................. A61M 5/14248 604/506 |
| 2015/0374919 A1 | 12/2015 | Gibson |
| 2016/0038689 A1 | 2/2016 | Lee et al. |
| 2016/0082182 A1* | 3/2016 | Gregory ............ A61M 5/14526 604/150 |
| 2016/0199574 A1 | 7/2016 | Ring et al. |
| 2016/0220798 A1* | 8/2016 | Netzel ............... A61M 5/14248 |
| 2016/0296704 A1 | 10/2016 | Gibson |

(Continued)

FOREIGN PATENT DOCUMENTS

| WO | 2018081234 A1 | 5/2018 |
| WO | 2018183039 A1 | 10/2018 |

(Continued)

*Primary Examiner* — Kevin C Sirmons
*Assistant Examiner* — Leah J Swanson
(74) *Attorney, Agent, or Firm* — Cook Alex Ltd.

(57) ABSTRACT

A drug delivery assembly is used for delivering a medicament to a patient. The assembly includes a main body having a housing and defining a recess, with an actuator associated with the housing. An adhesive pad, configured to attach to a human body surface, is associated with a lower surface of the housing. The assembly also includes a cartridge configured to be at least partially inserted into the recess and having: a cartridge housing, a drug reservoir positioned within the cartridge housing, a stopper movably associated with the drug reservoir, and a needle movably associated with the drug reservoir. The actuator is manipulated to deploy the needle, with the actuator also engaging the cartridge to prevent removal of the cartridge from the recess during drug delivery. A rod of the body engages the stopper to move the stopper and dispense a medicament from the drug reservoir during drug delivery.

26 Claims, 4 Drawing Sheets

(56) References Cited

U.S. PATENT DOCUMENTS

| | | |
|---|---|---|
| 2016/0354555 A1 | 12/2016 | Gibson et al. |
| 2017/0119969 A1 | 5/2017 | McCullough et al. |
| 2017/0124284 A1 | 5/2017 | McCullough et al. |
| 2017/0147787 A1 | 5/2017 | Albrecht et al. |
| 2017/0182253 A1 | 6/2017 | Folk et al. |
| 2017/0340837 A1 | 11/2017 | Nazzaro et al. |
| 2017/0361015 A1 | 12/2017 | McCullough |
| 2017/0368260 A1 | 12/2017 | McCullough et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0193557 A1* | 7/2018 | Johnson ............... A61M 5/158 |
| 2018/0256823 A1 | 9/2018 | Nazzaro et al. |
| 2018/0272059 A1 | 9/2018 | Marbet et al. |
| 2018/0304014 A1 | 10/2018 | Knudsen et al. |
| 2019/0022306 A1 | 1/2019 | Gibson et al. |
| 2019/0050375 A1 | 2/2019 | Fitzgibbon et al. |
| 2019/0060562 A1 | 2/2019 | Olivas et al. |
| 2019/0083702 A1 | 3/2019 | Nekouzadeh et al. |
| 2019/0134296 A1 | 5/2019 | Barbedette et al. |
| 2019/0143043 A1 | 5/2019 | Coles et al. |
| 2019/0143047 A1 | 5/2019 | Jazayeri et al. |
| 2019/0151544 A1 | 5/2019 | Stonecipher |
| 2019/0167908 A1 | 6/2019 | Fitzgibbon et al. |
| 2019/0192766 A1 | 6/2019 | Stonecipher |
| 2019/0247579 A1 | 8/2019 | Damestani et al. |
| 2019/0275241 A1 | 9/2019 | Ring et al. |
| 2019/0328965 A1 | 10/2019 | Moberg |
| 2019/0365986 A1 | 12/2019 | Coiner et al. |
| 2019/0374707 A1* | 12/2019 | Damestani ............... A61M 5/24 |
| 2019/0381238 A1 | 12/2019 | Stonecipher et al. |
| 2020/0023122 A1 | 1/2020 | McCullough et al. |
| 2020/0164145 A1 | 5/2020 | Chang et al. |
| 2020/0164155 A1 | 5/2020 | Mojarrad et al. |
| 2020/0179609 A1 | 6/2020 | Tan-Malecki et al. |
| 2020/0197628 A1 | 6/2020 | McCullough et al. |
| 2020/0206429 A1 | 7/2020 | Hering et al. |
| 2020/0230313 A1 | 7/2020 | Mojarrad et al. |
| 2020/0238004 A1 | 7/2020 | McCullough |
| 2020/0254172 A1 | 8/2020 | Forster et al. |
| 2020/0254185 A1* | 8/2020 | Bar-El ............... A61M 5/31535 |
| 2020/0261648 A1 | 8/2020 | Groszmann et al. |
| 2020/0261657 A1 | 8/2020 | Gibson et al. |
| 2020/0289745 A1 | 9/2020 | Harris et al. |
| 2020/0297927 A1 | 9/2020 | Conrath et al. |
| 2020/0322793 A1 | 10/2020 | Yang |
| 2020/0338271 A1 | 10/2020 | Harris et al. |

FOREIGN PATENT DOCUMENTS

| | | |
|---|---|---|
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

* cited by examiner

DRUG DELIVERY ASSEMBLY INCLUDING A REMOVABLE CARTRIDGE

BACKGROUND

Field of the Disclosure

The present disclosure relates to drug delivery devices. More particularly, the present disclosure relates to devices mounted to the body for automatically delivering a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, such devices integrate the drug reservoir into the housing of the device, which makes the device a single-use article that must be disposed of after use. Thus, it would be advantageous to provide a device configured to allow refill and/or reuse, rather than requiring removal and replacement of the device after every use.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a drug delivery assembly is disclosed. The assembly has a main body. The body includes a housing having upper and lower surfaces and defines a recess. The body also includes an actuator associated with the housing. An adhesive pad is associated with the lower surface of the housing. The adhesive pad is configured to removably attach to a human body surface. The assembly also has a cartridge. The cartridge includes: a cartridge housing, a drug reservoir positioned within the cartridge housing, a stopper movably associated with the drug reservoir, and a needle movably associated with the drug reservoir. The cartridge is sized and configured to be at least partially inserted into the recess. Furthermore, the body includes a rod configured to be engaged by the stopper when the cartridge is inserted into the recess. The actuator is configured to be manipulated to cause movement of at least a portion of the needle, with respect to the drug reservoir and/or a drug recipient.

Manipulation of the actuator moves a portion of the actuator into engagement with a portion of the cartridge so as to prevent removal of the cartridge from the recess.

In another aspect, a main body is provided for use in combination with a drug delivery cartridge of the type including a cartridge housing, a drug reservoir positioned within the cartridge housing, a stopper movably associated with the drug reservoir, and a needle movably associated with the drug reservoir. The main body includes a housing having upper and lower surfaces. The housing defines a recess configured to receive at least a portion of the drug delivery cartridge. The main body also includes a rod configured to engage the stopper of the cartridge when the cartridge is inserted into the recess. The main body also includes an actuator associated with the housing. The actuator is configured to be manipulated so as to cause movement of at least a portion of the needle of the cartridge with respect to the drug reservoir of the cartridge and/or a drug recipient. The actuator is further configured so that manipulation of the actuator moves a portion of the actuator into engagement with a portion of the cartridge so as to prevent removal of the cartridge from the recess. The body also includes an adhesive pad associated with the lower surface of the housing. The adhesive pad is configured to removably attach to a human body surface.

In another aspect, a drug delivery cartridge is provided for use in combination with a main body of the type including a housing defining a recess, a rod associated with the recess, an actuator associated with the housing, and an adhesive pad associated with the housing and configured to removably attach to a human body surface. The drug delivery cartridge includes a cartridge housing. The cartridge housing is sized and configured to be at least partially inserted into the recess of the main body. The cartridge also includes a drug reservoir positioned within the cartridge housing. The cartridge also includes a stopper. The stopper is movably associated with the drug reservoir and is configured to be engaged by the rod when the cartridge housing is inserted into the recess. Furthermore, the cartridge also includes a needle movably associated with the drug reservoir, wherein at least a portion of the needle is configured to be moved when the actuator of the main body is manipulated. Additionally, a portion of the cartridge housing is configured to engage a portion of the actuator of the main body when the actuator is manipulated, so as to prevent removal of the drug delivery cartridge from the recess.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
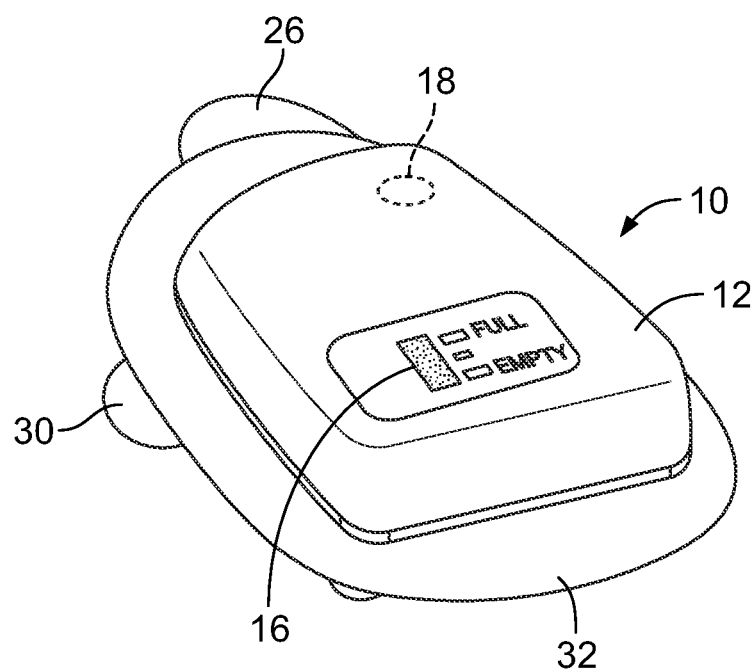
FIG. 1 is a top perspective view of a drug delivery device according to conventional design.
Figure 2:
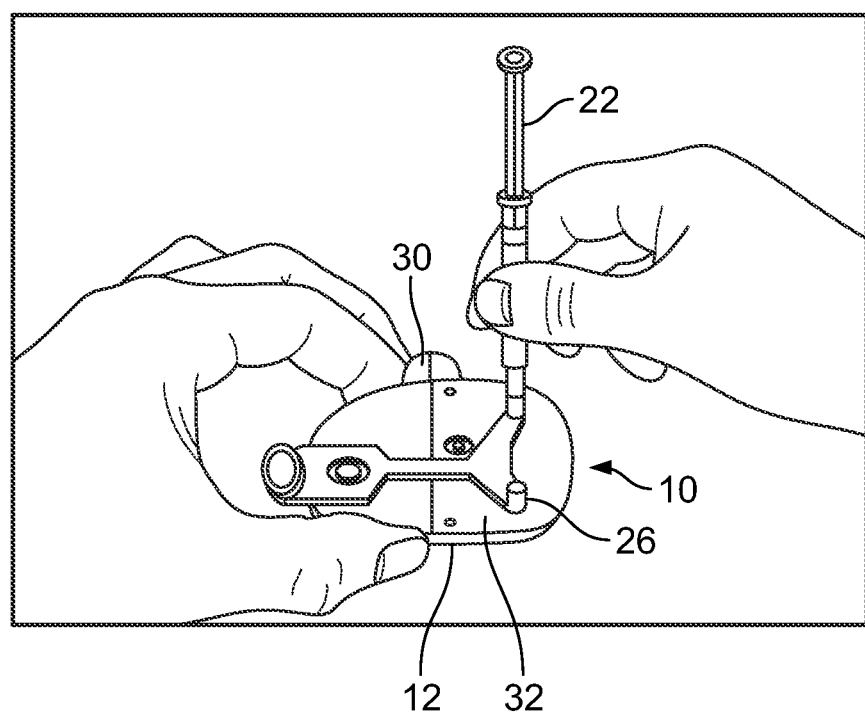
FIG. 2 is a bottom perspective view of the drug delivery device of FIG. 1.
Figure 3:
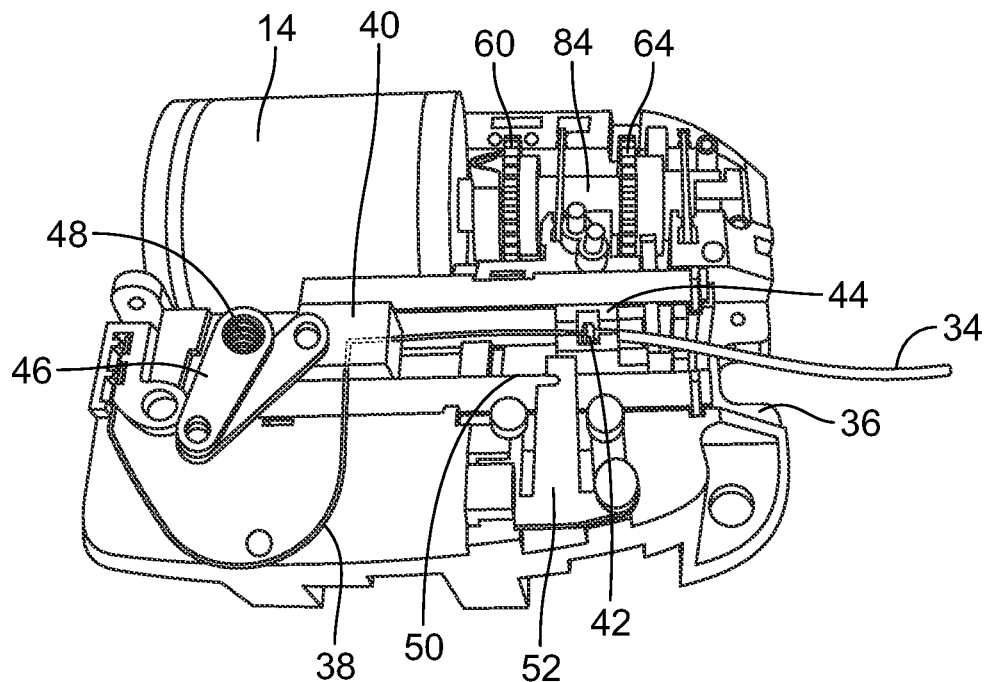
FIG. 3 is a top perspective view of the interior components of the drug delivery device of FIG. 1.
Figure 4:
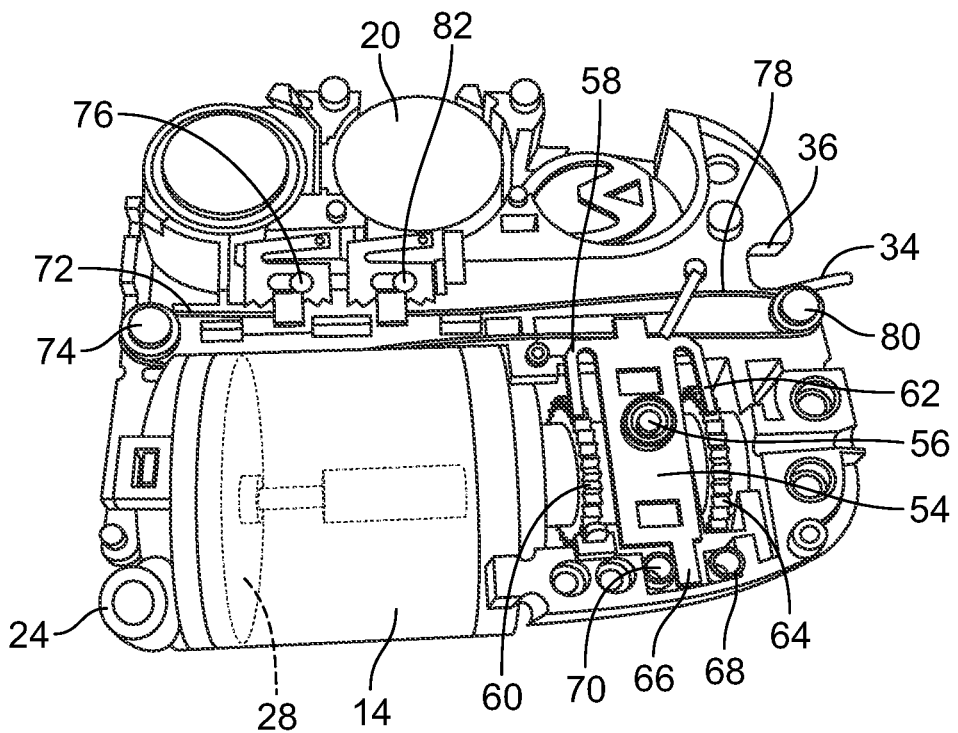
FIG. 4 is a bottom perspective view of the interior components of the drug delivery device of FIG. 1.
Figure 5:
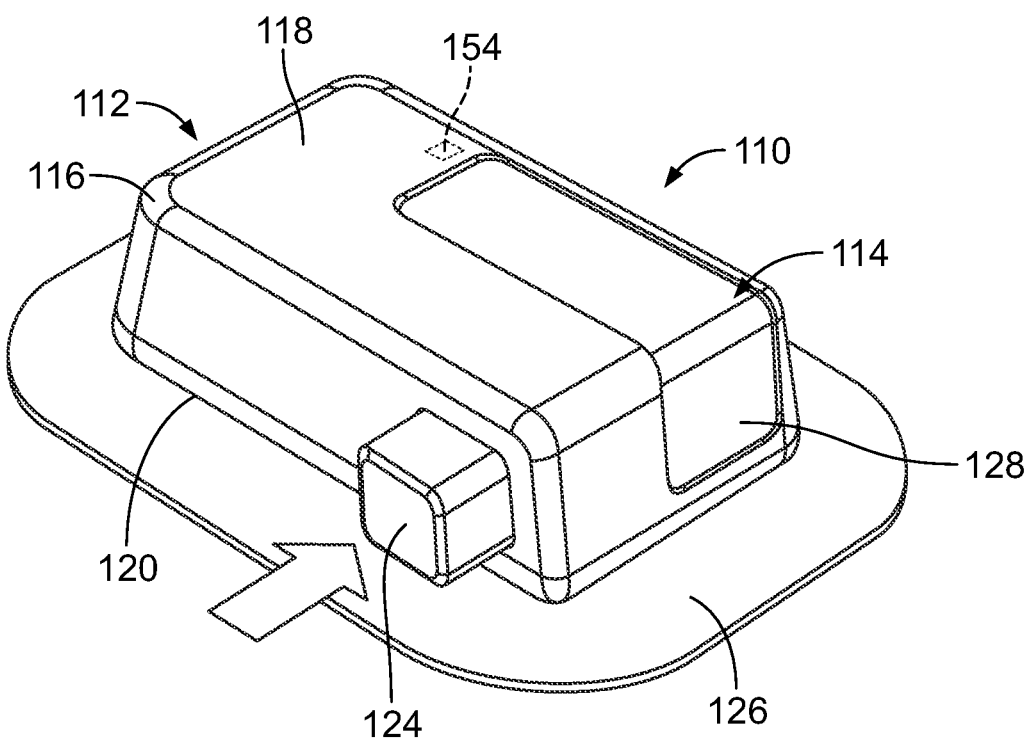
FIG. 5 is a top perspective view of an embodiment of a drug delivery assembly.
Figure 6:
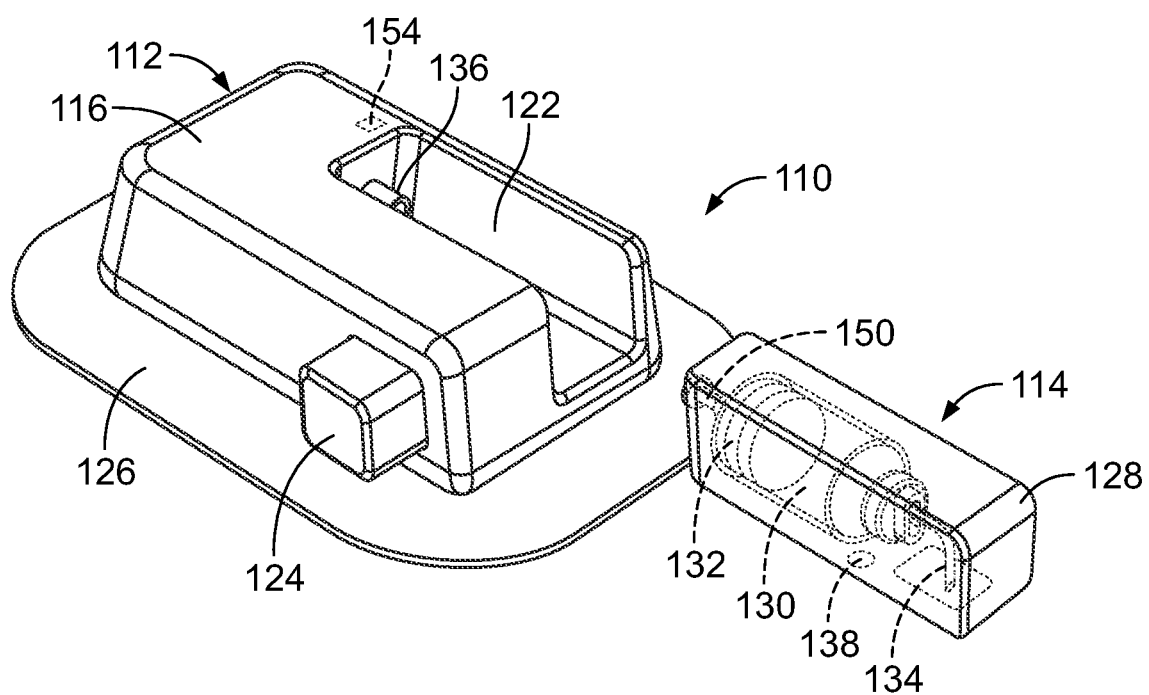
FIG. 6 is a top perspective view of the assembly of FIG. 5, showing a cartridge of the assembly separated from a main body of the assembly.

FIGS. 5 and 6 show an exemplary embodiment of a drug delivery assembly 110 according to the present disclosure. The assembly 110 includes a main body 112 and a cartridge 114. FIG. 5 shows the main body 112 and cartridge 114 coupled together and ready for use. FIG. 6 shows the cartridge 114 separated from the main body 112.

The body 112 includes a housing 116 having upper 118 and lower surfaces 120 and defining a recess 122 (FIG. 6) that is configured to at least partially receive the cartridge 114 (FIG. 5). The housing 116 may be made from any suitable (typically, generally rigid) material, including plastic polymers such as polyvinyl chloride (PVC), polypropylene, polycarbonate, and polystyrene. An adhesive pad 126 may be associated with the lower surface 120 of the housing 116. The adhesive pad 126 may be configured to removably attach to a human body surface. Any suitable medical grade adhesive pad configured to be removably attached to the human body surface may be used.

The cartridge 114 includes (as best shown in FIG. 6): a cartridge housing 128, a drug reservoir 130 positioned within the cartridge housing 128, a stopper 132 movably associated with the drug reservoir 130, and a needle 134 movably associated with the drug reservoir 130. The cartridge 114 is sized and configured to be at least partially inserted into the recess 122, as shown in FIG. 5. The body 112 also includes a rod 136 configured to be engaged by the stopper 132 when the cartridge 114 is inserted into the recess 122. The cartridge housing 128 may be made from any suitable material, including (for example) plastic polymers such as PVC. The drug reservoir 130 may also be made from any suitable material, including (but not limited to) polyethylene terephthalate (PET). The stopper 132 may be any suitably sized medical grade stopper, configured to form a fluid-tight seal against the inner surface of the drug reservoir 130, while also being movable along at least a portion of the length of the drug reservoir 130.

In an exemplary embodiment, the cartridge housing 128 may include a port 138 (FIG. 6) configured to receive a medicament. The port 138 may be incorporated into the cartridge housing 128, for example at the bottom or underside of the housing 128. The port 138 is configured to fluidically connect to the drug reservoir 130. To maintain sterility, a pierceable seal (not shown) may cover the port 138. The pierceable seal may be durable, such as a rubber septum, in order to seal the port to maintain sterility but allow for multiple refills. After entrance into the port 138, the medicament flows into the reservoir 130, in general accordance with the above description of the manner in which the reservoir 14 of the conventional device 10 of FIGS. 1-4 is filled. In such an embodiment, the drug reservoir 130 may be filled by a medical professional. The medical professional injects the medicament, for example using a syringe, through the port 138 and the medicament flows into the drug reservoir 130.

In all embodiments described herein, the medicament may be any suitable fluid medication. In an exemplary embodiment, the medicament may be pegfilgrastim, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

The medicament is most typically injected into the drug reservoir 130 immediately before the assembly 110 is secured to the patient to ensure that the proper drug is supplied, along with the proper amount. The drug reservoir 130 may be refillable, such that after the drug reservoir 130 is emptied upon first use, it may be filled again, for example by another injection. The drug reservoir 130 may be filled when the cartridge 114 is separated from the recess 122. Alternatively, the drug reservoir 130 may be filled when the cartridge 114 is attached to the recess 122.

In an alternative embodiment, the drug reservoir of the cartridge is not refillable, but is instead pre-filled with a medicament, for example during manufacture of the cartridge. In such an embodiment, the cartridge housing 128 may omit port 138, though it is also within the scope of the present disclosure for such a port 138 to be provided, but configured for only a single use (e.g., during manufacture to pre-fill the drug reservoir). Regardless of the particular configuration, after use, the cartridge is detached from the body and discarded. If further administration of a medicament is needed, a new pre-filled cartridge is coupled to the recess.

These pre-filled and fillable aspects allow the medicament to be stored separately from the assembly 110. For example, the medical professional may need to keep a drug at a certain temperature to retain the medicament's efficacy. The drug may be stored at the needed temperature, for instance cooled in a refrigerator or freezer until it is time for use, while the assembly 110 including the main body 112 and the empty or pre-filled cartridge 114 may be stored, for example, at room temperature.

As the medicament fills the drug reservoir 130, the stopper 132 moves (from right to left, in the orientation of FIG. 6) to accommodate the medicament. Movement of the stopper 132 into its final position (when the reservoir 130 has been filled with the appropriate amount of the medicament) causes an extension 150 of the stopper 132 to extend from the drug reservoir 130 (FIG. 6), allowing or causing the rod 136 to engage the extension 150 of the stopper 132. The rod 136 and extension 150 may be variously configured without departing from the scope of the present disclosure. For example, in one embodiment, the rod 136 may be configured as a push rod, configured to push the medicament through the reservoir 130 and into the needle 134 upon actuation of the assembly 110.

Figure 7:
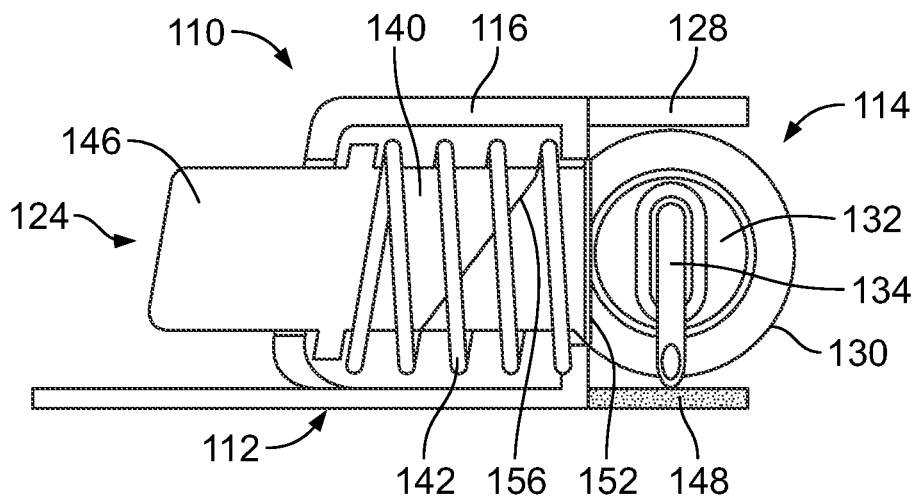
FIG. 7 is a detail view of an actuator and cartridge of the assembly of FIG. 5, showing the actuator in a first position.
Figure 8:
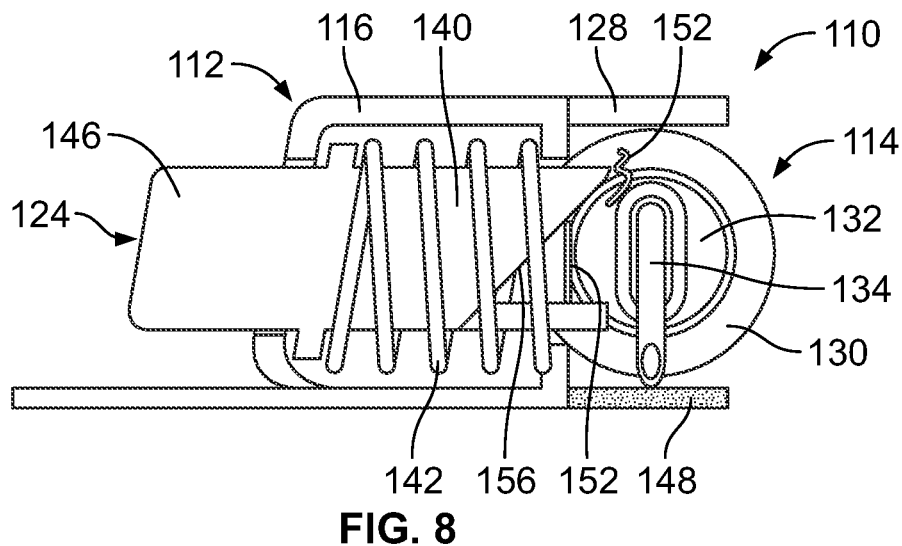
FIG. 8 is a detail view of the actuator and cartridge of FIG. 7, showing the actuator in an intermediate position.
Figure 9:
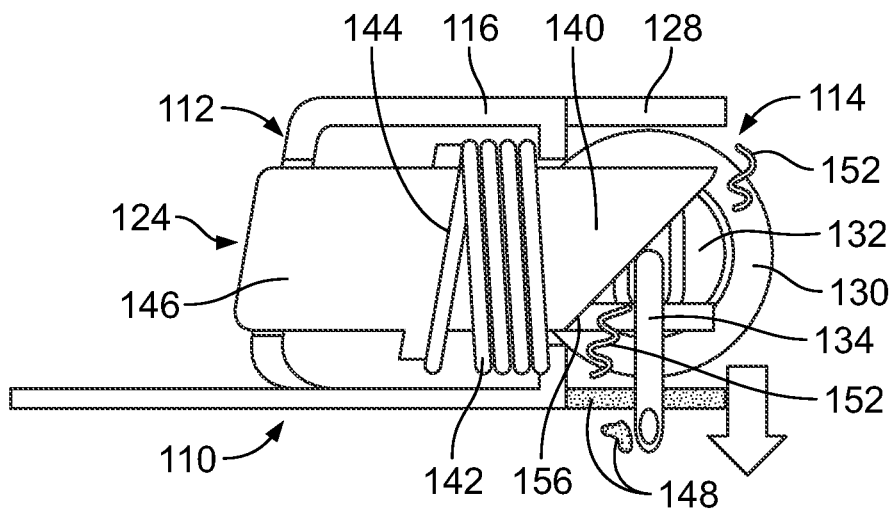
FIG. 9 is a detail view of the actuator and cartridge of FIG. 7, showing the actuator in a second position.

Turning back now to the body 112, it includes an actuator 124 associated with the housing 116. The actuator 124 is movable with respect to the housing 116, with FIGS. 7-9 showing the actuator 124 moving from a first position (FIG. 7), through an intermediate position (FIG. 8), and into a second position (FIG. 9). The actuator 124 may be variously configured without departing from the scope of the present disclosure. In the illustrated embodiment, the actuator 124 includes a button portion 146 at least partially positioned outside of the body housing 116. The illustrated actuator 124 also includes a cam or wedge 140 associated with the button portion 146. In the illustrated embodiment, the cam 140 is integrally formed with the button portion 146 as a single component, but it is within the scope of the present disclosure for the two to be separate components. The button portion 146 and the cam 140 may be made from any suitable, generally rigid material including, for example, PVC or a metallic material.

The cam 140 is surrounded by a coil spring 142 that bears against a portion of the button portion 146 and/or the cam 140 to bias the button portion 146 and cam 140 to the first position of FIG. 7, in which the cam 140 is spaced from the recess 122. The button portion 146 is pressed or otherwise manipulated to move it toward the housing 116 (in a left-to-right direction in the orientation of FIGS. 7-9), which compresses the spring 142 as the button portion 146 and cam 140 move toward the recess 122 (FIGS. 8 and 9), with at least a portion of the cam 140 eventually entering into the recess 122.

Before moving on to the implications of the cam 140 being at least partially moved into the recess 122, it is noted that the present disclosure is not limited to a manually manipulable actuator 124, but rather it is contemplated that the actuator 124 may be moved by any suitable means or mechanism. For example, rather than including a button portion 146 that is pressed to move the actuator 124 toward the recess 122, the actuator 124 may instead be configured to be moved by electrical and/or magnetic mechanisms.

Regardless of the particular mechanism employed to move the actuator 124, when the cartridge 114 is at least partially received within the recess 122, movement of the cam 140 into the recess 122 will cause the cam 140 to interact with the cartridge 114. In the illustrated embodiment, the cartridge 114 includes a sterile seal 152 that is oriented so as to be positioned in the path of the cam 140 when the cartridge 114 is mounted within the recess 122. The sterile seal 152 is configured to be pierced or otherwise broken by the actuator 124 when it is moved from the first position to the second position, such that it may be advantageous for the sterile seal 152 to be formed of a thin foil or film material that seals or overlays an opening defined in the cartridge housing 128 while being readily broken when contacted by the cam 140.

The cam 140 may include an inclined surface 156 configured to engage the sterile seal 152 when the actuator 124 is moved from the first position to the second position. If provided, the inclined surface 156 may facilitate piercing of the sterile seal 152, as shown in FIG. 8. In the illustrated embodiment, the inclined surface 156 is further configured to contact and cause movement of at least a portion of the needle 134 when the actuator 124 is moved into the second position, as shown in FIG. 9. In particular, the needle 134 is initially in a first position (which is shown in FIGS. 7 and 8 as a raised position) with respect to the drug reservoir 130 and the skin surface underlying the assembly 110. In one embodiment, the needle 134 may be out of fluid communication with the drug reservoir 130 when the needle 134 is in the first position, with the needle 134 only being placed into fluid communication with the drug reservoir 130 (e.g., with an outlet of the drug reservoir 130) when the needle 134 is moved into a second position by the inclined surface 156 of the cam 140 (FIG. 9). Alternatively, the needle 134 may be configured to be in fluid communication with the drug reservoir 130 regardless of the position of the needle 134, which may include the needle 134 being in fluid communication with the drug reservoir 130 before the cartridge 114 is mounted within the recess 122, or the needle 134 being placed into fluid communication with the drug reservoir 130 by the action of mounting the cartridge 114 into the recess 122 (e.g., by breaking a seal between the needle 134 and the drug reservoir 130).

As the inclined surface 156 of the cam 140 is pressed toward and against the needle 134, the inclined surface 156 will force the needle 134 to move from its first position to a second position, which is shown in FIG. 9 as a lowered position, which is closer to the lower surface 120 of the housing 116. The drug reservoir 130 may include a track or guide that defines the path of the needle 134 as the needle 134 is moved from the first position to the second position by the cam 140 (which is a vertical path, in the illustrated embodiment). In the second position, the needle 134 will be in fluid communication with the interior of the drug reservoir 130 to allow a medicament to be dispensed from the drug reservoir 130 via the needle 134. Additionally, in the second position, the needle 134 will pierce or otherwise pass through a lower seal 148 formed of a thin film or foil or the like that seals or overlays a lower opening defined in the cartridge housing 128. In embodiments in which the needle 134 is in fluid communication with the drug reservoir 130 before movement of the needle 134 into its second position, it may be advantageous for the lower seal 148 to be more substantial than a film or foil. For example, in such embodiments, the lower seal 148 may be configured as a rubber septum, with the end of the needle 134 positioned within the lower seal 148 when the needle 134 is in its first position (so as to prevent leakage of fluid from the needle 134), with movement of the needle 134 into its second position causing the end of the needle 134 to pierce entirely through the lower seal 148.

Regardless of the particular configuration of the lower seal 148, in the second position, the lower end of the needle 134 will extend out of the lower surface 120 of the housing 116 to pierce the skin of a patient to which the assembly 110 is secured by the adhesive pad 126. Thus, moving the actuator 124 from its first position to its second position will move the needle 134 from its first position to its second position, thereby creating a fluid flow path between the drug reservoir 130 and the patient, with the needle 134 defining at least a portion of the fluid flow path. While not shown in the illustrated embodiment, it should be understood that the assembly 110 may be provided with a cannula of the type described above with regard to the device 10 of FIGS. 1-4, with movement of the needle 134 with respect to the drug reservoir 130 causing deployment of a portion of the cannula into the skin of the patient, with one portion of the fluid flow path being by the needle 134 and another portion of the fluid flow path being defined by the cannula.

In an alternative embodiment, rather than the needle 134 being in fluid communication with the drug reservoir 130 before mounting the cartridge 114 into the recess 122, being placed into fluid communication with the drug reservoir 130 upon mounting the cartridge 114 into the recess, or being placed into fluid communication with the drug reservoir 130 by moving the needle 134 into its second position, the needle 134 may instead be configured to initially remain out of fluid communication with the drug reservoir 130 upon moving to the second position. In such an embodiment, some additional action or event following movement of the needle 134 into the second position causes the needle 134 to be placed into fluid communication with the drug reservoir 130. This subsequent action or event may comprise, for example, further movement of the actuator 124 or a secondary actuator to remove a seal between the needle 134 and the drug reservoir 130 (e.g., by causing an end of the needle 134 to pierce through a rubber septum positioned between that end of the needle 134 and the drug reservoir 130).

Once the needle 134 is in position to define at least a portion of the fluid flow path between the drug reservoir 130 and the patient, it is advantageous for the needle 134 to remain in place until a drug delivery routine has been completed. As the position of the actuator 124 determines the position of the needle 134, it may be advantageous to lock the actuator 124 in place during a drug delivery routine to ensure that the needle 134 remains properly positioned. Accordingly, the assembly 110 may be provided with a latch 144 (FIG. 9) that is actuated when the actuator 124 has moved into its second position. The latch 144 (which may be variously configured without departing from the scope of the present disclosure) engages a portion of the actuator 124 to prevent the compressed spring 142 from resiliently returning the actuator 124 from the second position to the first position. In one embodiment, a controller 154 of the assembly 110 configured to execute a drug delivery routine may execute a subroutine in which the latch 144 is deployed at the appropriate time; otherwise, the latch 144 may be configured to be automatically deployed via a suitable mechanical mechanism without involvement of the controller 154.

Locking the actuator 124 in place will lock the needle 134 in place. Locking the actuator 124 in place also serves to secure the cartridge 114 to the body 112. In particular, as shown in FIG. 9, when the actuator 124 is in its second position, the cam 140 will extend through the sterile seal 152 of the cartridge 114 and into an interior of the cartridge 114. With the actuator 124 in the second position, the cartridge 114 cannot be removed from the recess 122, due to the actuator 124 extending into the cartridge 114 and holding the cartridge 114 in place. Thus, locking the actuator 124 in place (in its second position) during a drug delivery routine will ensure the integrity of the fluid flow path during drug delivery (by holding the needle 134 in position) and ensure that the assembly 110 remains assembled during drug delivery. It should be understood that locking the actuator 124 in its second position is merely one possible approach to locking the cartridge 114 to the main body 112 and that additional or alternative mechanisms may be provided to lock the cartridge 114 in place within the recess 122. Likewise, locking the needle 134 in place may be achieved by a separate mechanism than the mechanism that locks the cartridge 114. The separate mechanism may be any appropriately configured locking mechanism, such as a latch.

While it is advantageous for the cartridge 114 and needle 134 to be locked in place during a drug delivery routine, it is advantageous for them to be moved once drug delivery has been completed. Thus, the assembly 110 may be configured such that the latch 144 will disengage the actuator 124 and allow the spring 142 to resiliently return the actuator 124 to its first or initial position after a drug delivery routine has been completed. The latch 144 may be actuated to disengage the actuator 124 at the appropriate time by any suitable approach, which may include the latch 144 being released as a result of a subroutine executed by the controller 154 or by the latch 144 being released by a suitable mechanical mechanism not requiring intervention by the controller 154. In either case, disengaging the latch 144 allows the spring 142 to resiliently return the actuator 124 from its second position to its first position. With the actuator 124 in its first position, the needle 134 may be returned to its first position and the cartridge 114 may be removed from the recess 122. The needle 134 should be removed from the skin of the patient before the cartridge 114 is removed from the recess 122 to prevent injury to the patient. To that end, it may be advantageous for the needle 134 to be configured to automatically move from its second position to its first position, such as by being spring-loaded, to ensure that the needle 134 has been removed from the patient before the cartridge 114 is removed from the recess 122. As an additional safety measure, the assembly 110 may include a secondary locking mechanism between the cartridge 114 and the main body 112 to better ensure that the needle 134 is retracted before the cartridge 114 is fully unlocked and allowed to be removed from the recess 122.

As for drug delivery using the assembly 110, in an exemplary embodiment, the controller 154 is configured to execute a drug delivery routine and is incorporated into the main body 112. The controller 154 may be variously configured without departing from the scope of the present disclosure, with the controller 154 being configured as a CPU or MPU of the type described above with regard to the controller of the device 10 of FIGS. 1-4. The controller 154 may be configured to be activated when the cartridge 114 is inserted into the recess 122 or when the actuator 124 is manipulated to move it from its first position to its second position or at any other suitable time. The exact nature of the drug delivery routine executed by the controller 154 may vary without departing from the scope of the present disclosure. For example, as described above, the controller 154 may be configured to execute a drug delivery routine in which a drug is delivered over the span of 45 minutes, with delivery beginning 27 hours after the controller 154 has been activated and applied to a patient (to ensure that the drug is not delivered sooner than 24 hours after a medical procedure or treatment).

Regardless of the particular steps carried out, each drug delivery routine will include at least a portion of the medicament in the drug reservoir 130 being conveyed out of the drug reservoir 130, through a fluid flow path at least partially defined by the needle 134, and into body of a patient. The flow of the medicament out of the drug reservoir 130 is controlled by movement of the stopper 132 through the drug reservoir 130. As described above, the stopper 132, when the cartridge 114 has been inserted into the recess 122, is coupled to a rod 136 of the main body 112. Movement of the rod 136 is controlled by the controller 154, which is coupled to the rod 136 by any suitable linkage (e.g., a muscle wire-lever assembly of the type described above with regard to the device 10 of FIGS. 1-4). During a drug delivery routine, the controller 154 causes the rod 136 to manipulate the stopper 132 to move through the drug reservoir 130 toward the needle 134, which dispenses medicament from the drug reservoir 130 via the needle 134.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A drug delivery assembly comprising:
a main body including
a body housing having upper and lower surfaces and defining a recess,
an actuator associated with the body housing, and
an adhesive pad associated with the lower surface of the body housing, the adhesive pad configured to removably attach to a human body surface; and
a cartridge including
a cartridge housing,
a drug reservoir positioned within the cartridge housing,
a stopper movably associated with the drug reservoir, and
a needle movably associated with the drug reservoir, wherein
the cartridge housing is sized and configured to be at least partially inserted into the recess,
the main body includes a rod configured to be engaged by the stopper when the cartridge housing is inserted into the recess, and
the actuator is configured to be manipulated to cause movement of at least a portion of the needle with respect to the drug reservoir and/or a drug recipient, with manipulation of the actuator moving a portion of the actuator into engagement with a portion of the cartridge so as to prevent removal of the cartridge from the recess.

2. The drug delivery assembly of claim 1, wherein the cartridge housing includes a port configured to receive a medicament, the port being fluidically connected to the drug reservoir, such that upon receipt by the port, the medicament flows into the drug reservoir.

3. The drug delivery assembly of claim 1, wherein the actuator includes an inclined surface configured to engage and cause movement of said at least a portion of the needle upon manipulation of the actuator.

4. The drug delivery assembly of claim 3, wherein the actuator includes a cam comprising said portion of the actuator that engages said portion of the cartridge so as to prevent removal of the cartridge from the recess upon manipulation of the actuator.

5. The drug delivery assembly of claim 3, wherein
the actuator further includes a spring encircling at least a portion of the actuator, and
the spring is configured to bias the actuator to a first position spaced away from the cartridge.

6. The drug delivery assembly of claim 5, wherein
the actuator is movable between the first position and a second position in which the actuator engages said portion of the cartridge so as to prevent removal of the cartridge from the recess upon manipulation of the actuator, and
the actuator includes a latch configured to prevent the spring from resiliently returning the cam from the second position to the first position.

7. The drug delivery assembly of claim 1, wherein
the actuator comprises a button portion at least partially positioned outside of the body housing, and
the actuator is configured to be manipulated by pressing the button toward the body housing.

8. The drug delivery assembly of claim 1, wherein the cartridge housing includes a sterile seal configured to be pierced by said portion of the actuator when the actuator is manipulated.

9. The drug delivery assembly of claim 1, wherein the cartridge housing includes a lower seal configured to be pierced by the needle upon said movement of said at least a portion of the needle with respect to the drug reservoir.

10. The drug delivery assembly of claim 1, further comprising a controller configured to execute a drug delivery routine, wherein the controller is configured to be activated upon the cartridge housing being inserted into the recess.

11. The drug delivery assembly of claim 1, further comprising a controller configured to execute a drug delivery routine, wherein the controller is configured to be activated upon manipulation of the actuator.

12. The drug delivery assembly of claim 1, configured to deliver pegfilgrastim to a drug recipient.

13. A main body for use in combination with a drug delivery cartridge including a cartridge housing, a drug reservoir positioned within the cartridge housing, a stopper movably associated with the drug reservoir, and a needle movably associated with the drug reservoir, the main body comprising:
   a body housing having upper and lower surfaces and defining a recess configured to receive at least a portion of the drug delivery cartridge;
   a rod configured to engage the stopper of the cartridge when the cartridge is inserted into the recess;
   an actuator associated with the body housing, the actuator configured to be manipulated so as to cause movement of at least a portion of the needle of the cartridge with respect to the drug reservoir of the cartridge and/or a drug recipient, with the actuator being further configured such that manipulation of the actuator moves a portion of the actuator into engagement with a portion of the cartridge so as to prevent removal of the cartridge from the recess; and
   an adhesive pad associated with the lower surface of the body housing, the adhesive pad configured to removably attach to a human body surface.

14. The main body of claim 13, wherein the cartridge housing includes a port configured to receive a medicament, the port being fluidically connected to the drug reservoir, such that upon receipt by the port, the medicament flows into the drug reservoir.

15. The main body of claim 13, wherein the actuator includes an inclined surface configured to engage and cause movement of said at least a portion of the needle upon manipulation of the actuator.

16. The main body of claim 15, wherein the actuator includes a cam comprising said portion of the actuator that engages said portion of the cartridge so as to prevent removal of the cartridge from the recess upon manipulation of the actuator.

17. The main body of claim 15, wherein
   the actuator further includes a spring encircling at least a portion of the actuator, and
   the spring is configured to bias the actuator to a first position spaced away from the cartridge.

18. The main body of claim 17, wherein
   the actuator is movable between the first position and a second position in which the actuator engages said portion of the cartridge so as to prevent removal of the cartridge from the recess upon manipulation of the actuator, and
   the actuator includes a latch configured to prevent the spring from resiliently returning the actuator from the second position to the first position.

19. The main body of claim 13, wherein
   the actuator comprises a button portion at least partially positioned outside of the body housing, and
   the actuator is configured to be manipulated by pressing the button toward the body housing.

20. The main body of claim 13, further comprising a controller configured to execute a drug delivery routine, wherein the controller is configured to be activated upon the cartridge housing being inserted into the recess.

21. The main body of claim 13, further comprising a controller configured to execute a drug delivery routine, wherein the controller is configured to be activated upon manipulation of the actuator.

22. The main body of claim 13, configured to deliver pegfilgrastim to a drug recipient.

23. A drug delivery cartridge for use in combination with a main body including a body housing defining a recess, a rod associated with the recess, an actuator associated with the body housing, and an adhesive pad associated with the body housing and configured to removably attach to a human body surface, the drug delivery cartridge comprising:
   a cartridge housing sized and configured to be at least partially inserted into the recess of the main body;
   a drug reservoir positioned within the cartridge housing;
   a stopper movably associated with the drug reservoir and configured to be engaged by the rod when the cartridge housing is inserted into the recess; and
   a needle movably associated with the drug reservoir, wherein
      at least a portion of the needle is configured to be moved when the actuator of the main body is manipulated, and
      a portion of the cartridge housing is configured to engage a portion of the actuator of the main body when the actuator is manipulated, so as to prevent removal of the drug delivery cartridge from the recess.

24. The cartridge of claim 23, wherein the cartridge housing includes a sterile seal configured to be pierced by said portion of the actuator when the actuator is manipulated.

25. The cartridge of claim 23, wherein the cartridge housing includes a lower seal configured to be pierced by the needle upon said movement of said at least a portion of the needle with respect to the drug reservoir.

26. The cartridge of claim 23, configured to deliver pegfilgrastim to a drug recipient.

* * * * *